(12) United States Patent
Mückter

(10) Patent No.: US 7,625,395 B2
(45) Date of Patent: Dec. 1, 2009

(54) IMPLANTABLE SCREW FOR STABILIZATION OF A JOINT OR A BONE FRACTURE

(75) Inventor: Helmut Mückter, Aachen (DE)

(73) Assignee: Novoplant GmbH, München (DE)

( * ) Notice: Subject to any disclaimer, the term of this patent is extended or adjusted under 35 U.S.C. 154(b) by 810 days.

(21) Appl. No.: 11/100,844

(22) Filed: Apr. 7, 2005

(65) Prior Publication Data

US 2005/0177167 A1    Aug. 11, 2005

Related U.S. Application Data

(63) Continuation of application No. 10/174,906, filed on Jun. 18, 2002, now abandoned.

(60) Provisional application No. 60/301,267, filed on Jun. 27, 2001.

(30) Foreign Application Priority Data

Jun. 21, 2001    (DE)    ................ 101 29 490

(51) Int. Cl.
  *A61B 17/84*    (2006.01)
(52) U.S. Cl. .................................... 606/300
(58) Field of Classification Search ............. 606/69–71, 606/74, 76, 77, 300–321; 411/383, 386, 411/392; 623/17.11–17.16
See application file for complete search history.

(56) References Cited

U.S. PATENT DOCUMENTS

| | | | |
|---|---|---|---|
| 4,947,502 A | | 8/1990 | Engelhardt |
| 4,959,064 A | | 9/1990 | Engelhardt |
| 5,061,137 A | * | 10/1991 | Gourd ........................ 411/510 |
| 5,152,790 A | | 10/1992 | Rosenberg et al. |
| 5,411,523 A | | 5/1995 | Goble |
| 5,518,351 A | * | 5/1996 | Peil ............................ 411/383 |
| 5,571,139 A | | 11/1996 | Jenkins, Jr. |
| 5,584,629 A | * | 12/1996 | Bailey et al. ................. 411/383 |
| 5,735,898 A | | 4/1998 | Braanemark |
| 5,814,047 A | | 9/1998 | Emilio et al. |
| 6,010,507 A | | 1/2000 | Rudloff |
| 6,190,411 B1 | | 2/2001 | Lo |
| 6,368,326 B1 | | 4/2002 | Dakin et al. |

(Continued)

FOREIGN PATENT DOCUMENTS

DE    299 15 204 U1    1/2000

(Continued)

OTHER PUBLICATIONS

"Die operative Behandlung der akuten, kompletten AC-Gelenksprengung" ("*Surgical treatment of acute, complete rupture of the AC Joint*") R.W. Fremerey et al., Unfallchirurg, Springer-Verlag 1996.

(Continued)

*Primary Examiner*—Thomas C Barrett
*Assistant Examiner*—Nicholas Woodall
(74) *Attorney, Agent, or Firm*—Henry M. Feiereisen; Ursula B. Day

(57)    ABSTRACT

A bone screw has a flexible shaft which prevents relative movements in the direction of tension, but permits smaller movements in all other directions. The bone screw is configured as a screw insertable into medullary cavities having a curved surface, where the screw adapts to the given contour.

7 Claims, 10 Drawing Sheets

U.S. PATENT DOCUMENTS

| | | | |
|---|---|---|---|
| 6,436,124 B1 | 8/2002 | Anderson et al. | |
| 6,908,275 B2 * | 6/2005 | Nelson et al. | 411/487 |
| 2002/0013623 A1 | 1/2002 | Sklar | |

FOREIGN PATENT DOCUMENTS

| | | |
|---|---|---|
| EP | 0 374 088 | 6/1990 |
| FR | 2 784 019 A | 4/2000 |
| FR | 2784019 A3 * | 4/2000 |

OTHER PUBLICATIONS

"Drahtseile und intraossäre Druckverteilungshülsen in der Chirurgie: ("*Wire cables and intrasseous pressure distribution systems in surgery*), R. Labitzke, Chirurg 53, Springer-Verlag 1982.

Claviculaplatten n. Wolter zur Behandlung der acromio-clavicularen Luxation , Waldemar Link, 1983.

"Syndesmosenhaken" ("*Syndesmosis hooks for treatment of tibiofibular syndesmosis ruptures*"), Engelbrecht, Waldemar Link, 1984.

* cited by examiner

IMPLANTABLE SCREW FOR STABILIZATION OF A JOINT OR A BONE FRACTURE

CROSS-REFERENCES TO RELATED APPLICATIONS

This application is a continuation of prior filed copending U.S. application Ser. No. 10/174,906, filed Jun. 18, 2002, now abandoned which claims the benefit of prior filed provisional application, Appl. No. 60/301,267, filed Jun. 27, 2001, pursuant to 35 U.S.C. 119(e), and which claims the priority of German Patent Application Serial No. 101 29 490.5, filed Jun. 21, 2001, pursuant to 35 U.S.C. 119(a)-(d).

BACKGROUND OF THE INVENTION

The present invention relates in general to an implant for augmenting stabilization of bone joints and in particular to an implant for augmenting stabilization of bone joints with a low relative movement and for interfragmentary stabilization of bone fractures, when primarily tensile forces are to be applied.

The joints of the body have different ranges of movement. In addition to the joints in the main axes of movement of the extremities as well as the mandibular joint, some of which have relative movements of a considerable extent, there are many joints with a low relative range of movement. Typical examples of this include the acromioclavicular joint as the connection between the shoulder blade and the collar bone (acromioclavicular joint), the joint between the collar bone and the breastbone or sternum (sternoclavicular joint), the iliosacral joint, the pubic symphysis, the articulated connections between the tibia and fibula (proximal and distal tibiofibular joints), the joints between the wrist (carpal bones) and the foot (tarsal bones) as well as the joints between the bones of the metacarpus (metacarpal joints) and those of the metatarsus (metatarsal joints). Likewise, injuries to these joints can in many cases lead to serious physical impairments, where a painful arthrosis develops as a result of a permanent joint incongruence. The therapeutic goal must therefore be to accurately reposition these joints and restore the capsule-ligament apparatus. In most cases, this cannot be accomplished by simply suturing the capsule-ligament apparatus. The sutures would not be able to withstand the stress and would rupture, and the joint would slip back into a false, incongruent position. Instead, the injured joint must be kept in a correct position through a suitable surgical implant by way of an augmentation until the capsule-ligament apparatus has healed to a sufficient level of strength and can again withstand the forces required to move the joint. The same thing is also true of unstable bone fractures, where an implant is supposed to keep the bones in the correct position, after repositioning the fracture, until the fracture has healed to an adequate level of strength.

Various techniques have been described for augmenting stabilization of a ruptured joint with small relative movements, and these techniques can be divided into roughly four groups: 1. temporary rigid bridging of the joint, 2. bridging with flexible implants, 3. retaining implants, which are bolted to one side of a joint and engage like a hook on the opposite side, 4. implants with an articular connection.

The best known representative of the first group (rigid implants) is the so-called locking screw. When using this principle, the two partners in the joint are secured rigidly relative to one another by a direct screw connection, which guarantees congruence of the joint, but blocks relative movement of the joint. Similar functions are achieved by bridging the joint with Kirschner's wires, optionally supplemented by wire cerclage or by using rigid osteosynthesis plates (especially in the area of the pelvis).

Known representatives of the second group (flexible implants) include plastic cords or bands made of absorbable or non-absorbable materials (literature: R. W. Fremerey et al. (1996) "Surgical treatment of acute, complete rupture of the AC joint," *Unfallchirurg* [Trauma Surgeon] 99:341-5), wire cables in the technique proposed by LABITZKE (literature: R. Labitzke (1982) "Wire cables and intraosseous pressure distribution systems in surgery," *Chirurg* [Surgeon] 53:741-3) or the use of wire cerclage.

Known representatives of the third group (screw-in implants with hooks) include hook plates proposed by Balser, Wolter or Dreithaler in a similar design for stabilization of ruptures of the acromioclavicular joint or the syndesmosis hooks developed by Engelbrecht (literature: E. Engelbrecht et al. (1971) "Syndesmosis hooks for treatment of tibio-fibular syndesmosis ruptures," *Chirurg* 42:92) for stabilization of ruptures of the ankle joint. These implants allow good augmentation of the joint and essentially preserve mobility, but it is difficult to adjust the proper congruence of the joint, which can often be achieved only by bending the implant subsequently, because these implants do not have any suitable possibilities for adjustment. In addition, a relatively large surgical access area is required, which necessitates a greater surgical trauma.

A typical representative of the fourth group (implants with an integrated joint) is the joint plate developed by Ramanzadeh for stabilization of ruptures of the acromioclavicular joint. However, this plate has the disadvantage that it is difficult to adjust the correct congruence of the joint, and the axes of rotation of the joint and the implant do not match, so the natural movement of the joint is at least partially blocked.

It would therefore be desirable and advantageous to provide an improved implantable screw for stabilizing a joint or a bone fracture to obviate prior art shortcomings.

SUMMARY OF THE INVENTION

According to one aspect of the present invention, this is achieved with an implant which augments the ligament connections reliably in joints with a small relative movement, while causing little or no impairment of the natural range of movement of the joint by providing an implantable screw which has a flexible shaft for stabilization of a joint or a bone.

The present invention resolves prior art problems by providing the design of an implant which guarantees a transfer of tensile forces almost exclusively, whereas there is little or no transfer of bending torque, compressive forces and transverse forces through the flexible shaft and by providing an implantable screw for stabilization of a joint or a bone fracture comprising an elongated body with a proximal head portion and a distal insertion portion having a thread, wherein the head portion and the insertion portion are interconnected by a flexible shaft.

The use of one or more such screws with a flexible shaft makes it possible to connect the bones involved in an unstable joint in such a way that there is little or no impairment of the natural joint movement.

Likewise, it is possible through the use of one or more such screws having a flexible shaft to apply primarily interfragmentary tensile forces when creating screw connections in bone fractures.

Such a screw makes it possible for both bones involved in a joint injury or both fragments involved in a bone injury to be joined by one or more screws which have a flexible shaft. This design of the implant guarantees transfer of tensile forces almost exclusively, while bending moments, compressive forces and transverse forces are not transmitted at all by the flexible shaft or only to a slight extent. In the case of capsule-ligament injuries of a joint, the screw is preferably installed so that the axis of the screw corresponds to the direction of the resultant force of the ligament connection of the joint. Ideal augmentation of the joint can be achieved in this way. In bone fractures, the screw is introduced at a right angle to the plane of the fracture and causes interfragmentary compression due to the tensile force.

Widening of the surgical space can be achieved to advantage through this invention. In an advantageous embodiment, this invention is suitable for a so-called minimally invasive implantation.

In addition, the screw according to this invention may be designed for use in surgery so that primarily tensile forces are transmitted but no significant bending moment is transmitted. Likewise, the screw according to this invention may be designed so that it can be introduced into the medullary cavity of a fractured bone by way of a so-called creep screw, thereby adapting to the contour of the medullary cavity, which is usually curved.

It is advantageous if the planar axial moment of inertia of the screw is 30% less, preferably more than 50% less than that of a screw having the same outside diameter.

The flexibility in the shaft area can be achieved by a wire cable, a wire bundle, a cord, a spiral or multiple webs and by fibers.

When using a wire cable or a wire bundle, it is especially advantageous if the wire cable or wire bundle is reinforced on the outside by sleeves or a spiral. Twisting of the wire cable or wire bundle is thereby limited when a torsional moment is applied, and thus the wire cable or wire bundle is stabilized. In addition, the bending movement of the shaft can be limited by the size of the sleeve or the spiral windings and their spacing relative to one another.

It is especially advantageous if the threaded part has a bone thread.

According to a preferred embodiment, the head part has a wrench socket and has a smooth surface or a bone thread matching the threaded part, depending on the intended application of the implant, said thread having a larger diameter and a smaller thread pitch than the bone thread in the threaded part.

With a high flexibility of the shaft and therefore inadequate transferability of the torsion moments required for the thread to penetrate, it is advantageous if the implantable screw has wrench sockets in the head part as well as in the threaded part. This allows a stepped wrench to act on these wrench sockets in synchronization.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 6b is a hexagon head wrench for use with the bone screw of FIG. 6a;

DETAILED DESCRIPTION OF PREFERRED EMBODIMENTS

Figure 1:
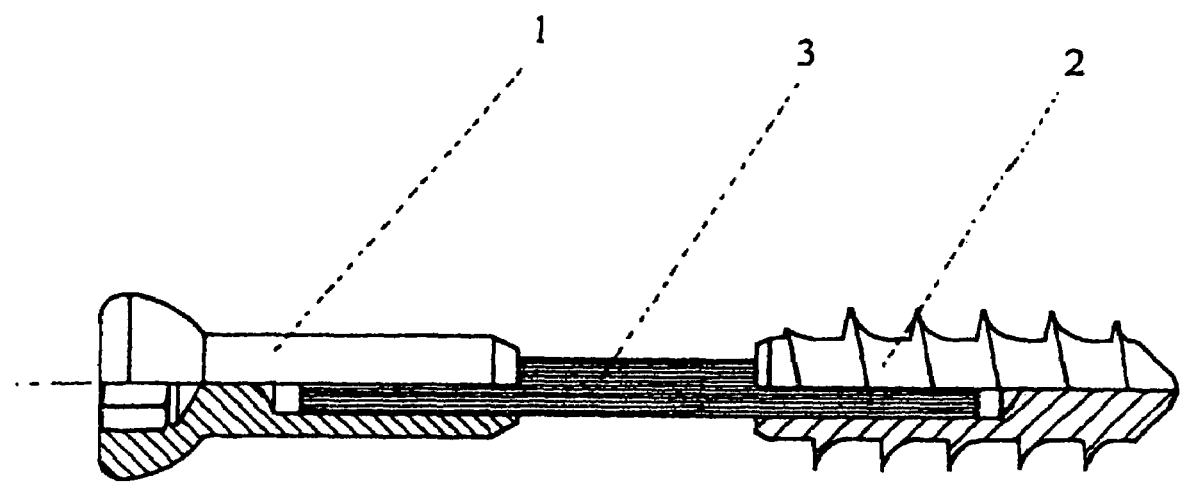
FIG. 1 is a bone screw according to the present invention, whose shaft is configured for flexibility as a wire cable or as a wire bundle.

Throughout all the Figures, same or corresponding elements are generally indicated by same reference numerals.

Turning now to the drawing, and in particular to FIG. 1, there is shown a bone screw, whose head part 1 and whose threaded part 2 are flexibly interconnected by a wire cable or a wire bundle 3. The wire cable or the wire bundle is fixedly connected in the head part as well as in the threaded part through suitable connection methods (e.g., pressed, glued, soldered or welded connections). The use of a wire cable or a wire bundle allows the application of tensile forces and the transfer of torsion moments by way of a flexible shaft. Compressive forces, transverse forces or bending moments, however, are transmitted only to a slight extent.

Figure 2:
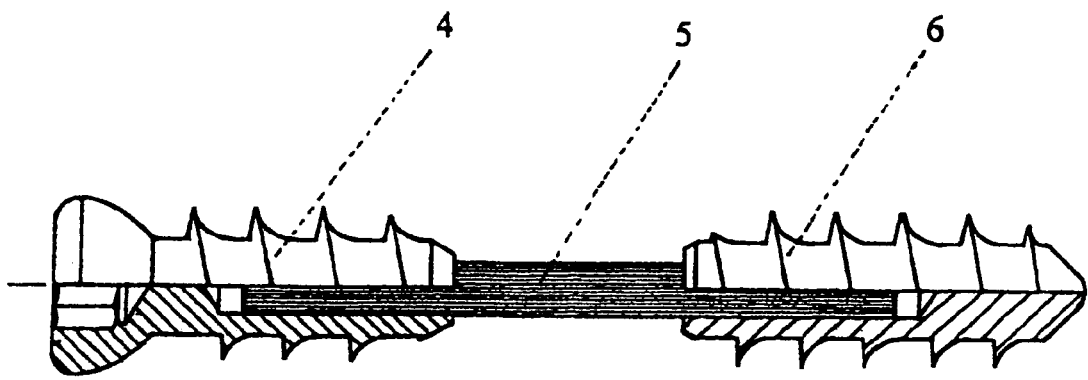
FIG. 2 is a bone adjusting screw, whose shaft is configured for flexibility as a wire cable or as a wire bundle.

FIG. 2 shows a bone locking screw which has a head part 4, which is provided with a bone thread, and a threaded part 6, which are flexibly interconnected by a wire cable or wire bundle 5 analogous to FIG. 1. The thread on the head part and the threaded part are of the same size and the thread flanks are the same. In this way, a previously defined distance between two bones to be joined is established, regardless of the tightening torque of the screw.

Figure 3:
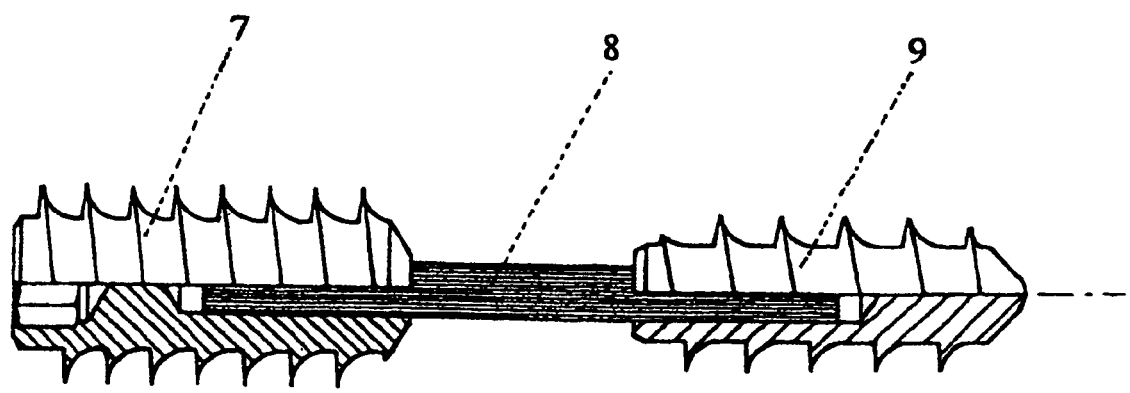
FIG. 3 is a bone screw, with a bone thread on the distal side from the head and whose shaft is configured for flexibility as a wire cable or as a wire bundle, with a bone thread at the proximal head side, which has a larger diameter and a smaller thread pitch than the bone thread distal from the head.

FIG. 3 shows a bone screw with a thread-bearing head part 7, which is flexibly connected to threaded part 9 by a wire cable or a wire bundle 8 analogous to FIG. 1. According to the known function principle of the Herbert screw, the thread on the head part has a larger diameter in comparison with the threaded part and it has a smaller thread pitch. When this screw is screwed into a fractured bone perpendicular to the plane of the fracture, the two fragments are moved toward one another and are braced against one another, where the extent of the movement toward one another per revolution of the screw is obtained from the difference between the two thread pitches.

Figure 4:
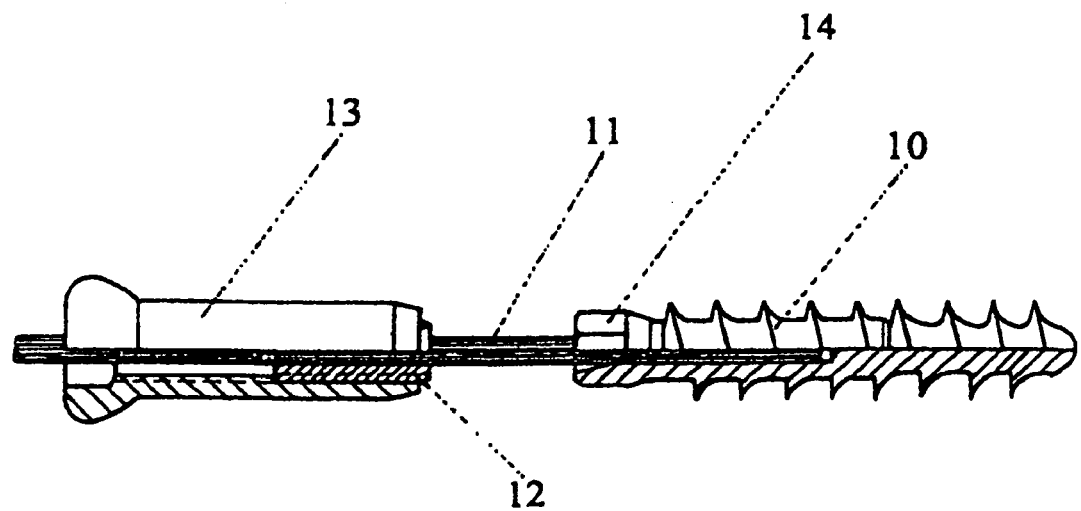
FIG. 4 is a screw, which has a bone thread on one side, with a shaft configured for flexibility as a wire cable, a cord or a wire bundle, and a bolt on the other side with a metal thread and a hexagon socket head nut screwed onto it.

FIG. 4 shows a screw which has a threaded part 10 on one side with a bone thread which is connected flexibly by a wire cable, a wire bundle or a cord 11 to a bolt 12, which has a metal or plastic thread. A hexagon socket head nut 13 is screwed onto this bolt. In implantation of such a screw, first the threaded part with the bone thread is screwed into the bone by way of a stud bolt. This is done by means of a cannulated wrench which is pushed over the wire cable or the wire bundle or the cord and the bolt and meshes with the hexagon insert bit 14 of the threaded part. Then the hexagon socket head nut is screwed onto the bolt with a metal thread by means of a cannulated hexagon socket wrench. Next, the wire cable or wire bundle that projects on the hexagon socket or the projecting cord is shortened with a knife forceps.

Figure 5:
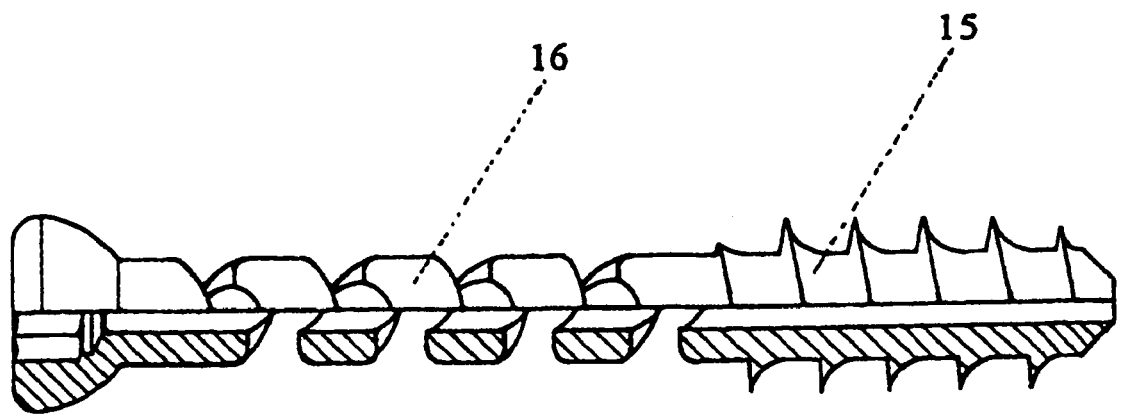
FIG. 5 is a bone screw, whose shaft is configured to be flexible in the manner of a spiral spring.

FIG. 5 shows a variation of a bone screw 15, whose shaft 16 is designed in the form of a spiral. In addition to the flexibility of the shaft, an elastic component is added in this variation. The amount of flexibility and elasticity of the shaft depends to a great extent on the design of the spiral. Large spirals have only a low flexibility and elasticity, whereas small spirals are highly elastic and flexible. Such a design variant is especially suitable for intramedullary screwing of bones with curved surfaces, e.g., as so-called creep screws in the area of the pelvis. The shaft length is limited by a wire cable, a wire bundle, a chain, a fiber or a flexible pin (not shown), preferably arranged in the spiral.

Figure 6A:
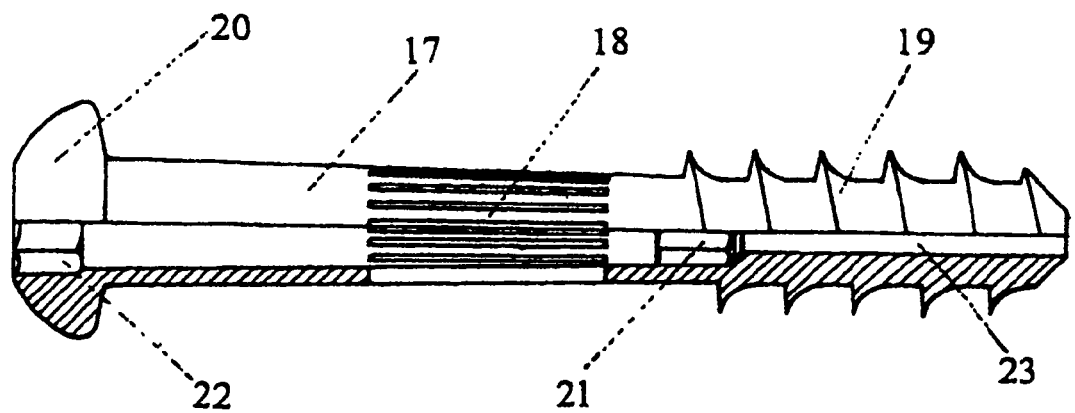
FIG. 6a is a bone screw, which is preferably made of a biocompatible plastic with a flexible shaft composed of multiple webs.
Figure 6B:
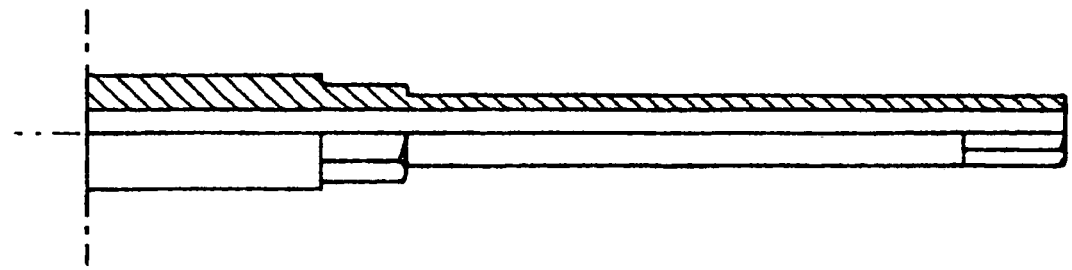

FIG. 6a shows a bone screw 17, which is preferably suitable for being fabricated from absorbable or non-absorbable plastics and is designed so that it can be manufactured by the casting technology. The flexibility of the shaft here is achieved due to the fact that it consists of multiple webs 18. The extent of the flexibility of this variant is defined by the number and dimensions of the webs and by the material properties of the material used. Since the webs are capable of transmitting the torsion moments which occur in tightening the screw only to a very limited extent, it is especially advantageous if a hexagon head 21, 22 (or a different type of wrench socket) is provided in both the threaded part 19 and the head part 20, so that a torsion load on the webs is prevented when using a corresponding stepped hexagon head wrench according to FIG. 6b. Likewise, it is advantageous for many applications if the threaded part is cannulated 23, so that application of the screw can take place through a corresponding guide wire.

Figure 7:
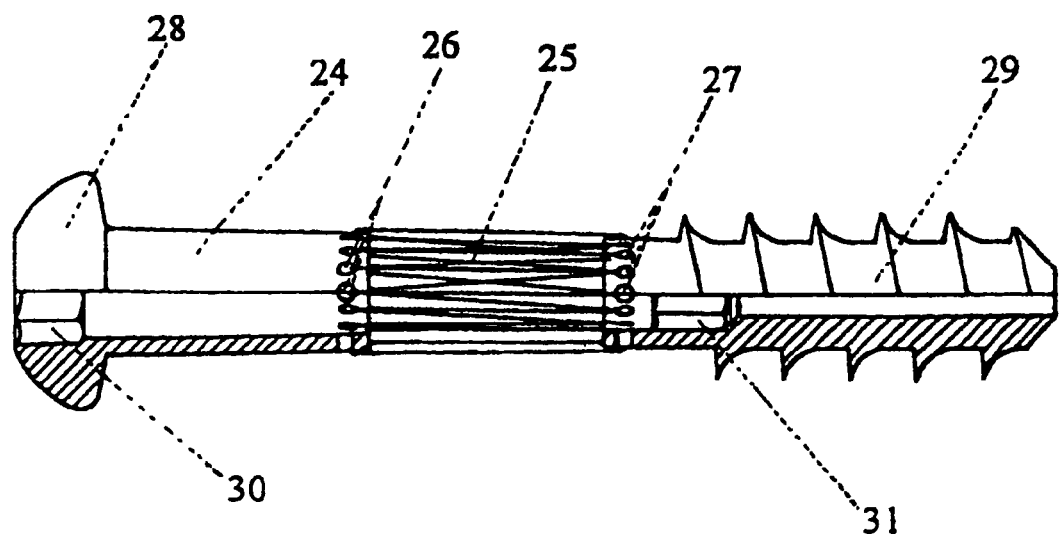
FIG. 7 is a bone screw, wherein the shaft consists of multiple fibers which are anchored alternately in the head part and in the threaded part of the bone screw.

FIG. 7 shows a bone screw 24, which is equally suitable for fabrication from an implant metal as well as from absorbable or non-absorbable plastics and which is designed so that the individual components can be manufactured by the casting technology. The flexibility of the shaft is achieved by the fact that it consists of multiple fibers 25 which are either held in eyelets 26, 27, anchored alternately in the head part 28 and in the threaded part 29 of the screw according to the figure or are each securely anchored in the head part and in the threaded part. Since this variant can transmit only tensile forces, a hexagon head socket 30, 31 (or a different type of wrench socket) is to be provided in both the head part and in the threaded part, analogous to FIG. 6a, permitting the use of a stepped wrench according to FIG. 6b, with which the head part and threaded part can be screwed equally into the bone.

Figure 8:
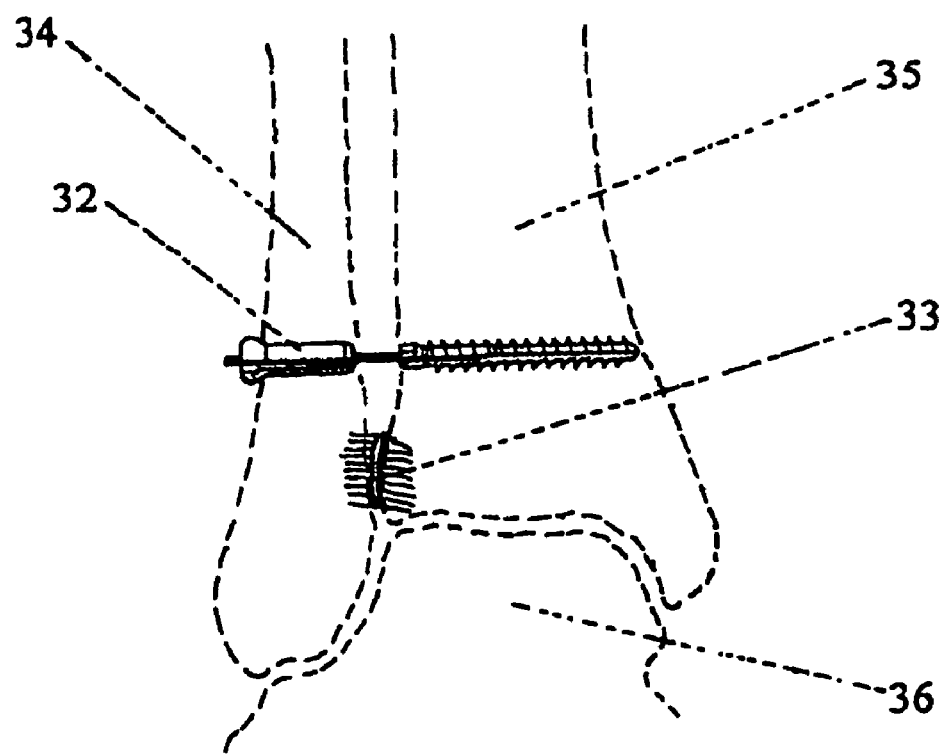
FIG. 8 is an embodiment of a bone screw according to the present invention for stabilization of the ankle joint (distal tibiofibular joint, syndesmosis)

FIG. 8 shows an embodiment of a bone screw with a flexible shaft 32 according to FIG. 4, which is introduced into the area of the ankle for augmentation of a ruptured syndesmosis 33 (syndesmosis=ligament connection between the fibula 34 and the tibia 35 in the area of the ankle joint). In contrast with a conventional rigid screw connection, the natural relative movement between the fibula and tibia is preserved due to the flexible shaft. However, it is impossible for the ankle to yield, which would lead to instability of the ankle bone 36. The dimensions of the bone screw are selected so that it can be introduced into the bone through the boreholes in a conventional osteosynthesis plate when there is a concomitant fracture of the lateral malleolus.

Figure 9:
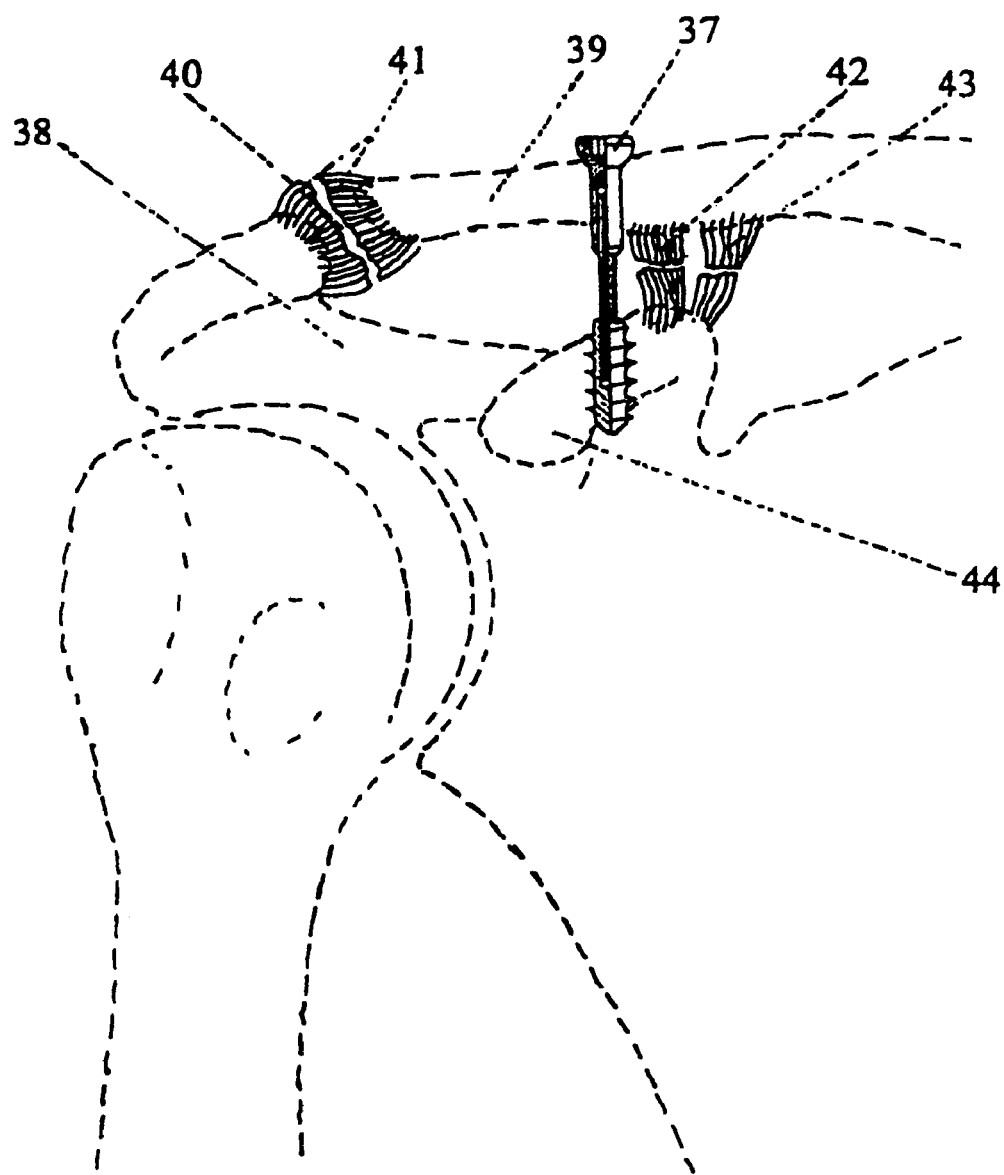
FIG. 9 is a further embodiment for stabilization of the acromioclavicular joint.

FIG. 9 shows another embodiment of a bone screw with a flexible shaft 37 according to FIG. 1 in the area of the ligament connection between the shoulder blade 38 and the collar bone 39, on the acromioclavicular joint 40. The rupture of all three ligaments involved in this connection is diagramed schematically (acromioclavicular ligament 41, trapezoid ligament 42, conoid 43). According to the principle described in 1941 by Bosworth for the use of rigid screws, the screw is screwed into the coracoid process 44 through the collar bone. In contrast with a conventional rigid screw connection, the natural relative movement between the collar bone and the shoulder blade is maintained due to the flexible shaft. However, a high position of the collar bone, which would lead to incongruence of the acromioclavicular joint, is impossible.

Figure 10:
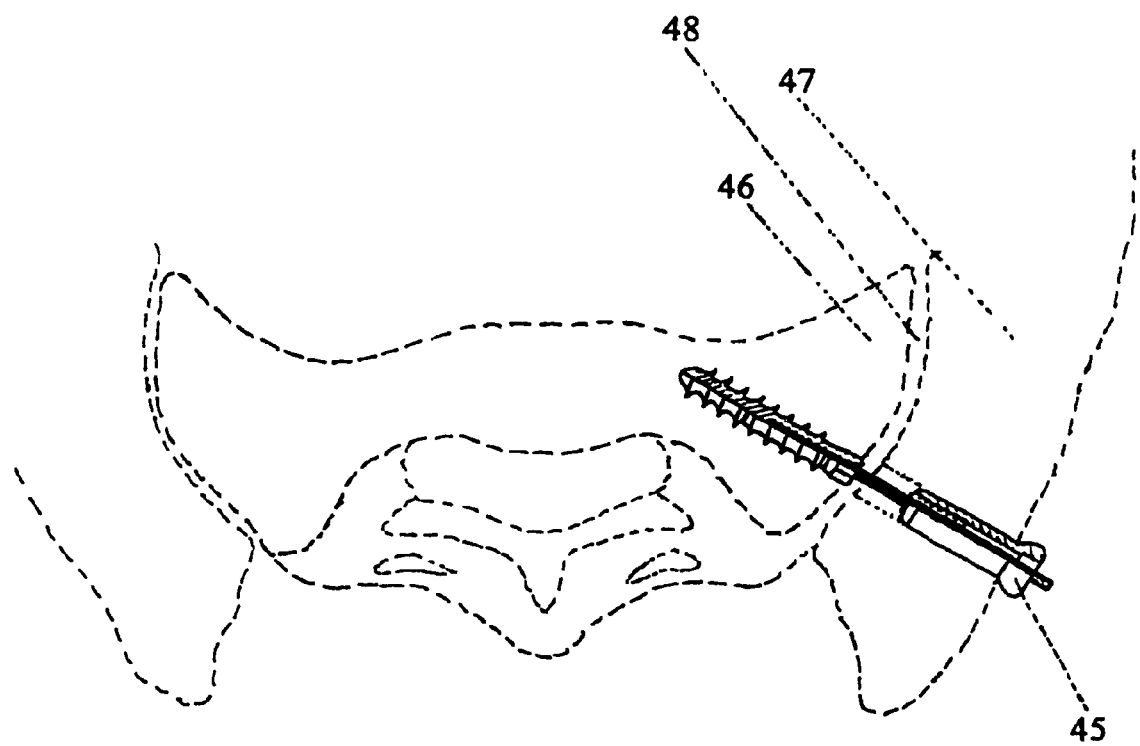
FIG. 10 is another embodiment for stabilization of the iliosacral joint.

FIG. 10 shows another embodiment of a bone screw having a flexible shaft 45 according to FIG. 4 in the area of the ligament connection between the sacrum 46 and the iliac bone 47 (iliosacral joint 48). In the case of an instability of the posterior pelvic ring due to injury, stabilization is accomplished by screwing one or more screws with a flexible shaft into the bone. In contrast with a conventional rigid screw connection, the natural relative movement between the sacrum and the ileum is preserved due to the flexible shaft. However, gaping of the joint gap is reliably prevented due to the screw having a flexible shaft.

Figure 11:
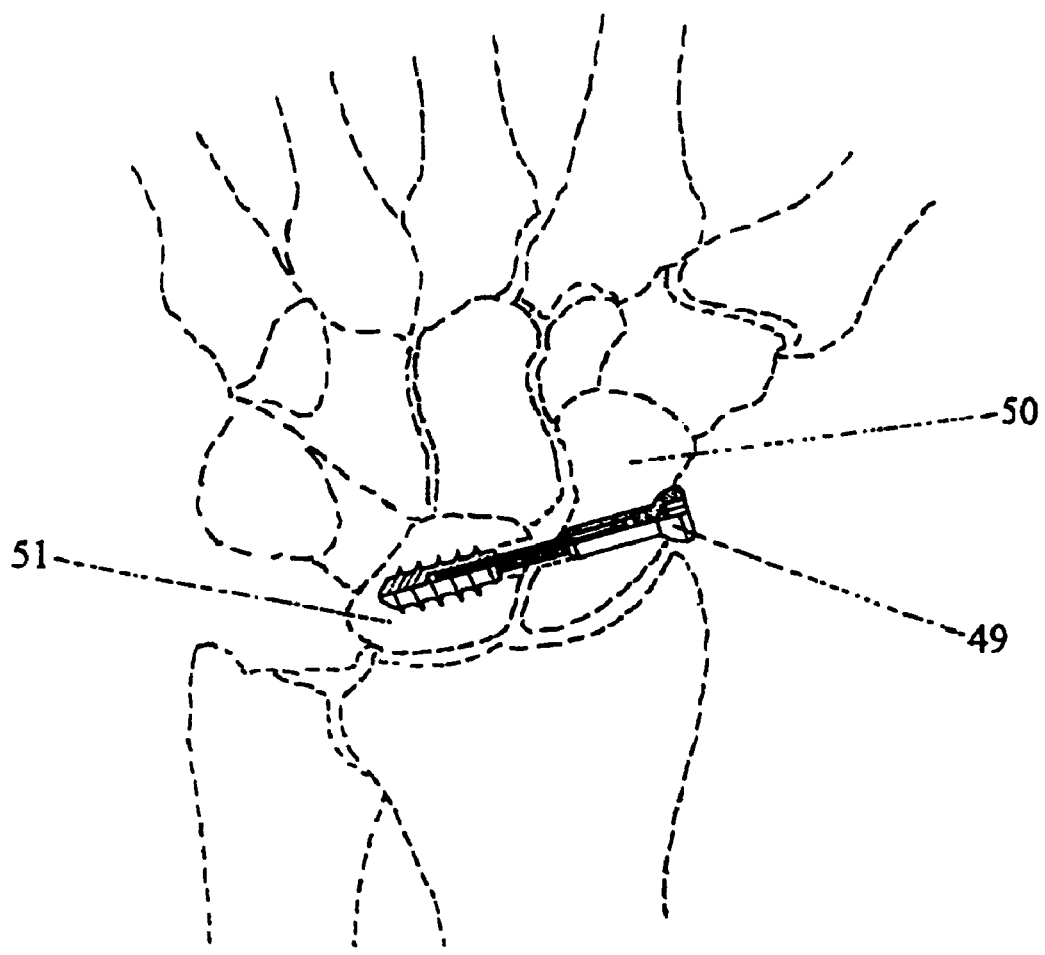
FIG. 11 is another embodiment for stabilization in the area of the wrist with scapholunate dissociation.

FIG. 11 shows another embodiment of a bone screw having a flexible shaft 49 according to FIG. 4 in the area of the wrist in the case of a ruptured ligament between the scaphoid bone 50 and the lunate bone 51 (scapholunate dissociation). Repositioning and stabilization are accomplished by screwing a screw having a flexible shaft into the bone. In contrast with a conventional rigid screw connection or stabilization with Kirschner's wires, the natural relative movement between the scaphoid bone and the lunate bone is preserved due to the flexible shaft. However, the wrist bones that have been screwed together cannot yield laterally.

Figure 12:
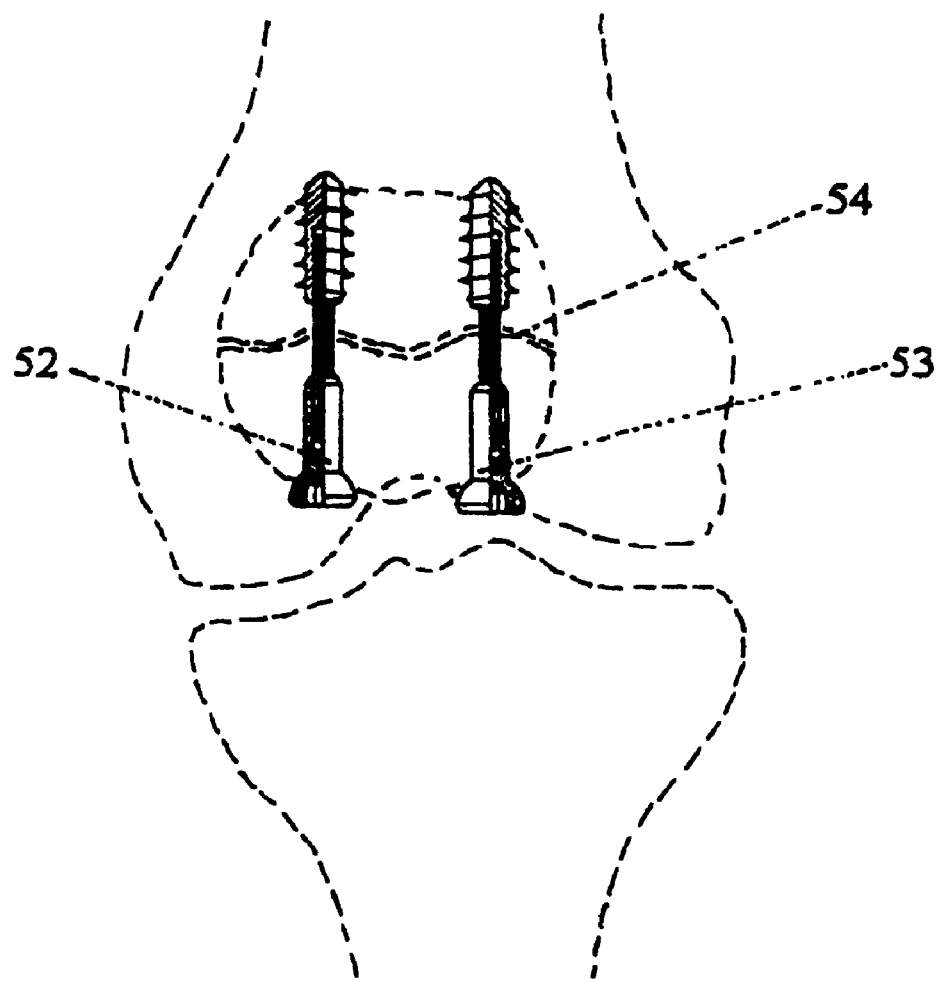
FIG. 12 is yet another embodiment for interfragmentary traction screws in the area of the patella with a fracture of the patella.

FIG. 12 shows another embodiment of bone screws with a flexible shaft 52, 53 according to FIG. 1 with a transverse fracture of the patella 54. According to the known tension belt principle, the tensile forces conducted from the quadriceps tendon over the patella and into the patellar tendon are transferred through the two bone screws with a flexible shaft and the two fragments of the patella are compressed together.

Figure 13:
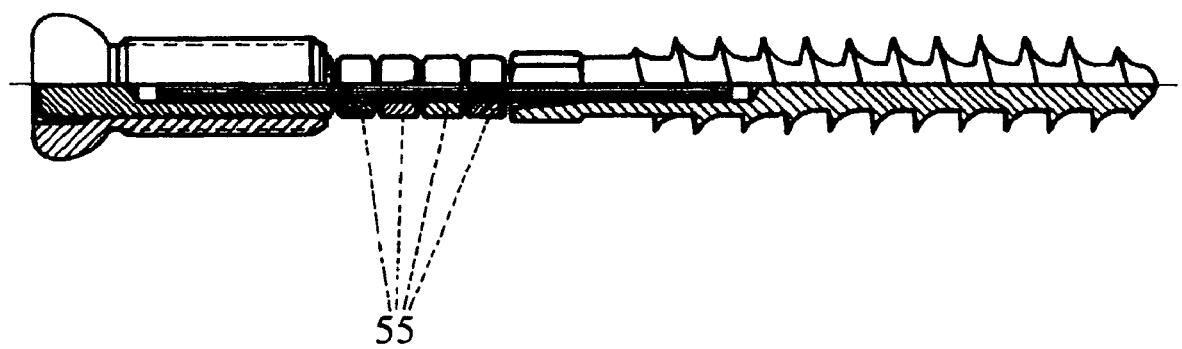
FIG. 13 is a bone screw according to FIG. 4, where the wire cable or the wire bundle is reinforced by individual sleeves.

FIG. 13 shows a bone screw according to FIG. 4, where wire cable or wire bundle is reinforced by individual sleeves 55. In accordance with their winding, wire cables tend to twist and coil up when a torsion moment is introduced in the opposite direction to their winding. Due to the fact that sleeves or a spiral are pushed onto the wire cable or the wire bundle, this twisting can be limited, and at the same time, a stabilization of the wire cable can be achieved due to the resulting clamping of the wire cable in the sleeve or the spiral. This allows higher torsion moments to be transmitted than is possible with an unreinforced wire cable or wire bundle. In addition, depending on the design of the sleeve and the spacing of the individual sleeves or spiral windings relative to one another, the extent of the bending of the flexible screw shaft can be limited.

While the invention has been illustrated and described as embodied in an implantable bone screw for a joint or bone fracture, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A screw implant for stabilization of a joint or a bone fracture, comprising:
    a screw including a head portion on one end;
    a threaded portion on another end; and
    a shaft portion extending between the head portion and the threaded portion and defining an axis, wherein the shaft portion is constructed in the form of a wire cable comprised of several wire strands and constructed sufficiently flexible to maintain a natural movement of bone participants in an area of the joint or bone fracture but rigid enough to prevent an elongation in a direction of the axis away from one another;
    wherein the threaded portion includes a bone thread and a nut connected in one piece with the bone thread for attachment of an external wrench to screw the threaded portion into one of the bone participants, and
    wherein the head portion includes a bolt connected to the shaft portion and a nut screwed onto the bolt and provided for attachment of an external wrench for securement of the head portion in the other one of the bone participants.

2. The screw implant of claim 1, wherein the wire strands are arranged in spaced-apart relationship along a major portion of the axis.

3. The screw implant of claim 1, wherein the nut is a hexagon nut.

4. The screw implant of claim 1, wherein the head portion is a bolt having a socket for attachment of an external wrench for securement of the head portion in the other one of the bone participants.

5. The screw implant of claim 4, wherein the socket is a hexagon socket.

6. The screw implant of claim 1, and further comprising a reinforcement placed from outside over the shaft portion.

7. The screw implant of claim 6, wherein the reinforcement is at least one sleeve or a spiral.

* * * * *